United States Patent [19]

Carriere et al.

[11] Patent Number: 4,905,504
[45] Date of Patent: Mar. 6, 1990

[54] FOAM PULSE RHEOMETER

[75] Inventors: Craig J. Carriere, Midland, Mich.; David H. Bank, Lake Jackson, Tex.; Christopher P. Christenson, Lake Jackson, Tex.

[73] Assignee: The Dow Chemical Company, Midland, Mich.

[21] Appl. No.: 323,647

[22] Filed: Mar. 15, 1989

[51] Int. Cl.⁴ ............................................. G01N 11/10
[52] U.S. Cl. ........................................................ 73/60
[58] Field of Search ........................ 73/59, 60, 54, 64.4

[56] References Cited

FOREIGN PATENT DOCUMENTS 18742 2/1981 Japan ........................................ 73/60

Primary Examiner—John Chapman
Assistant Examiner—Joseph W. Roskos
Attorney, Agent, or Firm—Thomas J. Burger; David S. Stallard; Timothy S. Stevens

[57] ABSTRACT

A foam pulse rheometer measures the total integrated stress response of a foaming polymer to a short duration strain pulse applied to the polymer, from which can be calculated the equilibrium modulus and the zero shear viscosity of the foaming polymer during the foaming reaction. A shear plate mounted to a load cell above a jacket extends downwardly into a foaming polymer within the jacket. Under the application of a vertical square wave strain pulse to the jacket, the load cell senses the shear force exerted upon the shear plate by the foaming polymer. Simultaneously, a video camera and recorder monitors the surface area of the plate acted upon by the jacket. For each pulse, simultaneously occurring discrete sensed force values and discrete monitored surface area values can be used to compute the total integrated stress response, from which can be calculated the equilibrium modulus and the zero shear viscosity. By applying successive strain pulses during the foaming process, until the polymer tears away from the plate, the evolution of the equilibrium modulus can be studied throughout the course of the foaming reaction.

27 Claims, 6 Drawing Sheets

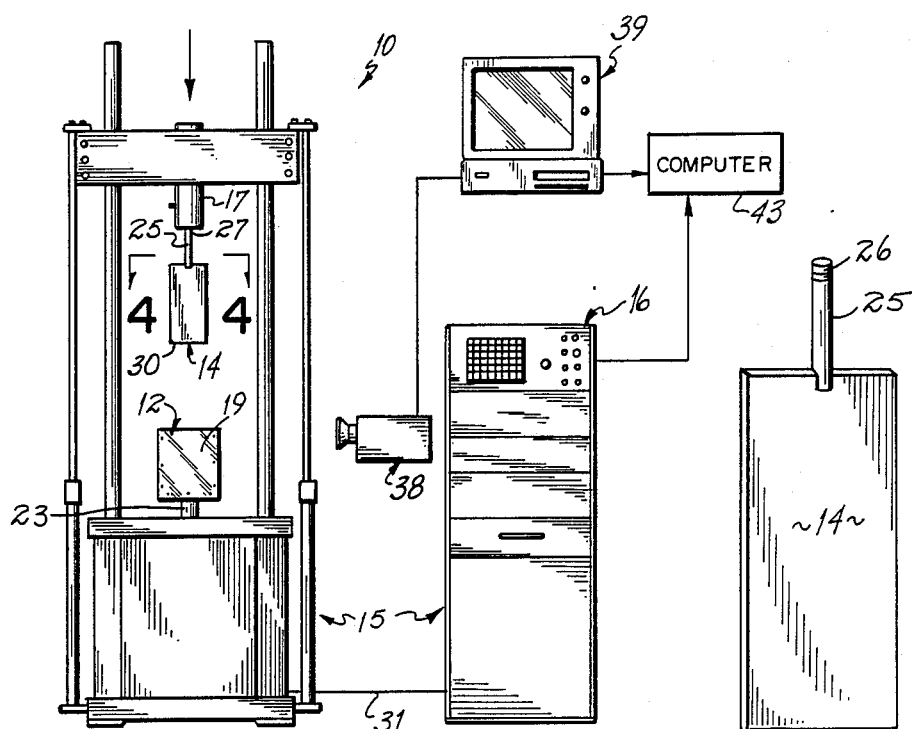
FIG. 1
FIG. 3
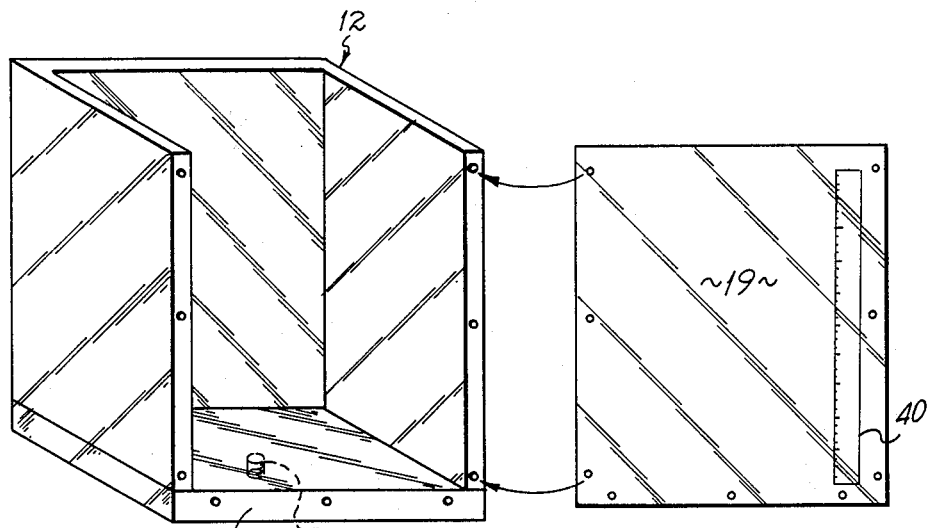
FIG. 2

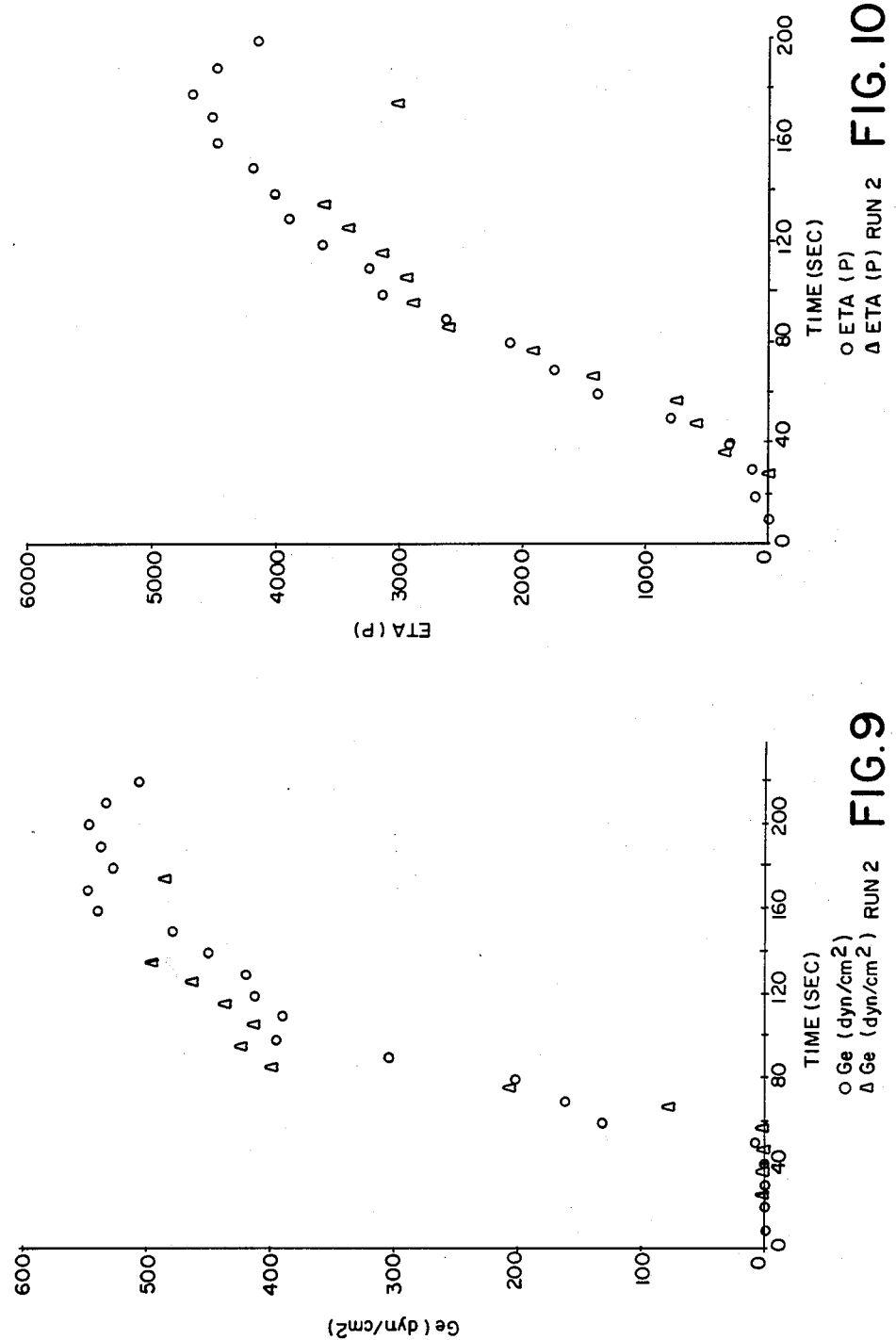

FOAM PULSE RHEOMETER

FIELD OF THE INVENTION

This invention relates to apparatus and methods for measuring certain parameters attendant the process of a foaming reaction of a polymer. More particularly, the invention relates to apparatus and methods useful for determining the equilibrium shear modulus and the zero shear viscosity of a foaming cellular polymer during various stages in the foaming reaction.

BACKGROUND OF THE INVENTION

Cellular polymers or foams, are multiphase materials that consist of a polymeric matrix and a fluid phase that is typically a gas. Most polymers can be expanded into a foam, but few have been commercially exploited. The two most widely used foam materials in terms of volume are polyurethanes and polystyrenes. Structurally, the cellular polymer system can be described as having either an open-cell or closed-cell geometry. In closed cell foams, the fluid is dispersed in the form of discrete gas bubbles and the polymeric material forms a continuous phase. In open-cell foams, the voids coalesce so that the solid and fluid phases form a continuous network structure.

Foams represent an important class of engineering materials. Because of their low density, excellent mechanical and thermal properties, these materials have been used in a wide variety of applications. Although the majority of modern applications for cellular polymers utilize solid foams, the final product is obtained by processing a liquid foam, e.g., mold filling process, where an understanding of the rheology of the foam is critical.

Rheology is the study of the flow of materials, particularly the plastic flow of solids and the flow of non-Newtonian liquids. If the rheological properties, such as equilibrium modules and zero shear viscosity, of a foaming polymer during the foaming reaction can be determined, an assessment of the evolving flow characteristics, for instance, the mold filling capability, of the polymer can be ascertained. This provides information as to whether or not a particular polymer could be used in a particular process or application, or information on how to improve pre-existing processes already using the polymer.

Despite the widespread use of cellular polymers, only a very limited amount of information exists on the rheological properties of foams, and that is to say, the equilibrium modules and the zero shear viscosity. The majority of the work to date consisted of continuum mechanics-based models for a cellular polymer after the final structure has been formed, or on the load-compression properties of the final foam. Virtually no known work has been done on the aforesaid rheological properties of the liquid cellular polymer during the transient or foaming process. This is largely due to the absence of a reliable rheological instrument capable of handling the unique problems associated with a foaming polymer.

Current commercial rheometer designs are not easily adapted for use with foaming polymers for several reasons. First, the foaming process is a transient process, involving a large volume expansion that is typically ten to twenty times the volume of the original components. This material expansion problem alone eliminates the majority of traditional rheometer designs, which are designed to measure only single phase systems, or are closed system in-line devices.

Secondly, the foaming reaction is quite rapid. Typically, the entire reaction takes two to three minutes. Also, the properties of the foam are changing constantly throughout the foaming reaction. This means that the rheological data must be acquired rapidly. Another problem that must be addressed is the drastic variation in solution viscosity that occurs during the course of the foaming reaction. The viscosity of the foam can change from several poise to several thousand poise in a few minutes.

In an article entitled "Determination of Time Independent Component of the Complex Modulus During Cure of Thermosetting Systems," published in the July 1983 edition of *Polymer Engineering and Science*, and expressly incorporated by reference herein in its entirety, authors Richard J. Farris and Charles Lee describe an impulse approach to linear visco-elasticity with respect to Narmco 5208 epoxy resin. The impulse approach can be used to separate elastic from viscoelastic contribution to the equilibrium modulus, and to determine whether a material under investigation is a viscoelastic liquid or an elastic solid from the absence or the presence of the equilibrium modulus. This impulse approach, using parallel plates in torsion, has been used to follow the change in the modulus of the Narmco 5208 epoxy resin having a structure that is evolving with time. However, this resin does not generate foam during thermosetting, and there is no suggestion in the article as to how the impulse approach could be used to measure the rheological properties of expanding foam polymers during the foaming reaction.

It is thus one objective of this invention to provide apparatus and methods for measuring and determining certain rheological properties of a foaming cellular polymer during the foaming process.

SUMMARY OF THE INVENTION

This invention contemplates apparatus and methods for measuring rheological properties of a foaming cellular polymer during the foaming reaction. In a preferred embodiment, this is accomplished by measuring the total integrated shear stress response of a foaming polymer to an applied strain pulse input, from which the equilibrium modulus and the zero shear viscosity for the foaming polymer during the pulse can be calculated. By applying successive strain pulses throughout the course of the foaming reaction, and by measuring the total integrated shear stress response for each pulse, the equilibrium modulus and the zero shear viscosity for each pulse can be calculated and the evolution of the rheological properties of the polymer during foaming can be studied.

In a preferred embodiment the total integrated shear stress response of a foaming polymer to a strain input is measured or determined by sensing the shear force imparted upon a shear plate immersed in the foaming polymer during the strain pulse and by simultaneously monitoring, with a video recorder, the total surface area of the shear plate that is immersed in the foaming polymer and subject to the shear force. The sensed force values and the monitored surface area values are matched up for a selectable number of discrete data points occurring during the pulse, and are then substituted into equations derived from the impulse approach in order to calculate the equilibrium modulus and the zero shear viscosity. Accordingly, the rheological properties of a foaming cellular polymer are followed by video recording the surface area of the shear plate immersed in the foaming polymer during the pulse while simultaneously sensing the shear forces on the plate, thereby accounting for the transient effects of rapid, large volume expansion during the foaming reaction.

More particularly, in accordance with a preferred embodiment of the invention, a foam pulse rheometer includes a transparent jacket into which a foaming polymer is introduced. An actuator rod driven by a programmable controller vertically displaces the jacket in a succession of square wave pulses applied during the foaming reaction. For each pulse, the jacket moves up a specified distance, remains in place for a specified pulse duration, and then moves back downward to its original position. A shear plate mounted above the jacket extends downwardly into it and remains immersed in the foaming polymer during the foaming reaction. A load cell connected to the shear plate senses the shear force imparted upon the shear plate by the foaming polymer at selected points in time during each pulse, the sensed values being stored in a controller. A video camera and recorder monitors the height of the foaming polymer in the jacket, thereby to provide values corresponding to the amount of surface area of the plate that is sheared by the foam. For a discrete number of data points during each pulse, the simultaneously occurring monitored surface area values are matched with the sensed force values in order to obtain a discrete number of stress response values. From these values, by integrating, the total integrated shear stress response can be computed for each pulse. From the total integrated stress response, the equilibrium modulus and the zero shear viscosity can be calculated. By carrying out this calculation for a number of successive pulses, until the foam becomes fairly solid and tears away from the plate, sufficient data can be obtained to follow the evolution of both the equilibrium modulus and the zero shear viscosity throughout the foaming process.

Preferably, the controller enables an operator to select the amount of vertical displacement of the rod, the rate of displacement of the rod, the duration of the pulse and the elapsed time between successive pulses. For each square wave pulse, the controller also stores the values for vertical displacement of the rod, the duration of the pulses, and the sensed force values for a selectable number of discrete points in time during each pulse.

The transparent jacket is box-shaped and preferably has a removable face plate with a ruler designation demarcated thereon, thereby facilitating precise measurement of the height of the foaming polymer in the jacket. The shear plate is preferably machined of aluminum, and has a sharpened bottom edge to reduce compressive loading. The controller is programmed with a data acquisition and control program that allows the operator to choose the vertical displacement of the jacket, the displacement rate, the data acquisition rate, i.e., the number of discrete test points, and the pulse duration. A listing of the source code of this program is identified as Table II at the end of the detailed description.

The data stored by the MTS controller, along with the data from the video recorder, is then input into a separate computer which utilizes a data analysis routine to calculate the stress for each discrete data point during the pulse. It then calculates a base line and performs an integration of the stress response for each pulse, using the trapezoidal rule with successively occurring discrete stress response values being the bases of each trapezoid, and the time between data points being the height of the trapezoid. From the total integrated stress for the pulse, the equilibrium modulus and the zero shear viscosity can be calculated. A listing of the source code for this program is identified as Table III at the end of the detailed description.

The rheometer of this invention may be advantageously employed to measure the rheological properties of a wide variety of cellular polymeric materials during the foaming reaction. These cellular polymers include flexible urethanes, which are typically used in cushioning applications, rigid urethanes (or rigid isocyanurate systems) which are typically used in insulation applications, and others, such as phenol formaldehyde.

These and other features of the invention will be more readily understood in view of the following detailed description of the drawings and the drawings in which:

BRIEF DESCRIPTION OF THE DRAWINGS

FIG. 1 is a schematic illustrating a foam pulse rheometer in accordance with a preferred embodiment of the invention;

FIG. 2 is a disassembled perspective view showing the transparent outer jacket used in the preferred embodiment of the invention;

FIG. 3 is a perspective view of a shear plate used in a preferred embodiment of the invention;

FIG. 9 is a plot of the equilibrium modulus versus time for two free rise polyurethane foams at room temperature;

FIG. 10 is a plot of the zero shear viscosity versus time for two free rise polyurethane foams at room temperature.

DETAILED DESCRIPTION OF THE DRAWINGS

Figure 4:
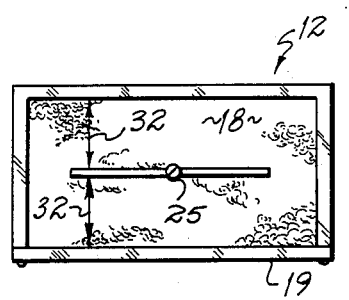
FIG. 4 is a sectional view taken along lines 4—4 of FIG. 1, but showing a foaming polymer in the jacket.

To understand the invention, it is necessary to briefly summarize the impulse approach, mentioned earlier, to the theory of linear viscoelasticity. The constitutive equation for a linear, isotropic, incompressible, and nonaging viscoelastic material can be transformed into the following equation:

$$\int_0^\infty \tau_{yx}(t)dt = G_e \int_0^\infty \gamma_{yx}(t)dt + \gamma_{yx}(\infty)\eta_o \quad \text{Equation (1)}$$

where $\tau_{yx}$ and $\gamma_{yx}$ are the y-x components of the deviatoric stress and strain dyadics, respectively. The left side of the equation is the total stress impulse and the right side contains the equilibrium modulus, $G_e$, multiplied by the total strain impulse and the product of the zero shear viscosity, $\eta_o$, and the magnitude of the strain at infinite time.

If the strain pulse is such that the starting and ending strain states are the same, i.e., $\gamma_{yx}(\infty)=0$, then Equation (1) reduces to $$G_e = \int_0^\infty \tau yx(t)dt / \int_0^\infty \gamma yx(t)dt \quad \text{Equation (2)}$$

The equilibrium modulus, $G_e$, is made of both time dependent (elastic) and time independent (visco-elastic) components. However, when the strain impulse is such that the strain at long times is zero, the impulse approach can then be used to separate elastic from visco-elastic contributions, since the time dependent modulus $G(t)$ does not appear in Equation (2). If the total strain impulse is zero and the beginning and ending strains are the same, i.e., a full sine wave, then the total stress impulse must also be zero regardless of whether the material is viscous, elastic, or viscoelastic. If the material under investigation is a viscous or viscoelastic liquid, then the equilibrium modulus is zero, since the system can relieve any imposed stress by flowing. Therefore, under those conditions, Equation (1) reduces to $$\int_0^\infty \tau yx(t)dt = \eta_o \gamma yx(\infty). \quad \text{Equation (3)}$$

From these types of experiments one can check the assumptions of linearity and determine whether the material under investigation is a viscoelastic liquid or an elastic solid from the absence or presence of the equilibrium modulus.

In practice, the integrations of the stress and strain can only be carried out over a finite amount of time. Thus, the equations for the equilibrium shear modulus and the zero shear viscosity reduce to:

$$G_e \cong \int_0^{\delta t} \tau yx(t)dt / \int_0^{\delta t} \gamma yx(t)dt \text{ if } \gamma yx(\infty) = 0 \quad \text{Equation (4)}$$

$$\eta_o \cong \int_0^{\delta t} \tau yx(t)dt / \gamma yx(\delta t) \text{ if } G_e = 0 \quad \text{Equation (5)}$$

where $\delta t$ is the duration of the strain input. Clearly, the values calculated for the equilibrium modulus and the zero shear viscosity are approximate.

FIG. 1 depicts a foam pulse rheometer 10 in accordance with a preferred embodiment of the invention. The rheometer 10 includes a transparent outer jacket 12, a shear plate 14, and a testing unit 15 that is equipped with data acquisition hardware and software. Preferably, this testing unit 15 is provided by The Materials Testing Services Corporation of Minneapolis, Minn. ("MTS"). An MTS Series 810 catalog, expressly incorporated by reference herein in its entirety, describes the capabilities of the various testing units of this type. The software for the testing unit 15 is preferably written in MTS BASIC. The unit 15 also includes a controller 16, a load cell 17, and an actuator rod to be described later. For this invention, any load cell 17 providing force sensing capabilities within the range of ±25 lbs. would be suitable. The controller 16 may be selected from suitable components shown and described in Series 810 materials Test System Catalog so long as these components provide square wave vertical displacement capability. The frame supports the load cell 17 and the shear plate 14. The load cell 17 supports the shear plate 14 above the jacket 12, so that the shear plate 14 extends downwardly into contact, or immersed in, a foaming cellular polymer 18 in the jacket 12.

The jacket 12 is preferably made of ½" thick transparent panels, has an internal volume of about 4 liters, and is box-shaped, with internal horizontal dimensions of about 8"×4", and a vertical height of about 10". Preferably, as shown in FIG. 2, one side wall of the jacket 12 comprises a detachable transparent face plate 19. The bottom, or base, 20 of the jacket 12 is 9"×4½", with about 1.5" thickness. Centered in the base 20, an internally threaded tap 22 is sized to threadably receive a vertically displaceable actuator rod 23 that forms part of the MTS testing unit 15.

The shear plate 14 is mounted to the load cell 17 by a cylindrical shaft 25 that is externally threaded at its top end 26 into a bore 27 formed in the load cell 17. The bottom end 29 of the shaft 25 is notched and heli-arc welded to the plate 14. The dimensions of the plate 14 are preferably 5"×12", with a thickness of about ⅛". The bottom 30 of the shear plate 14 is machined to a sharp edge to avoid compressive loading. Initially, the bottom 30 is located about one inch from the base 20 of the jacket 12, so as to avoid contact during the downstroke. Initially, the bottom 30 is located about an inch from the base 20, so as to avoid contact between the plate 14 and the jacket 12 during the downstroke. Preferably, both the shear plate 14 and shaft 25 are made of aluminum. Except for the above-described threaded connection, the recited dimensions should be within about ±0.3".

The controller 16 is connected to the actuator rod 23 by a cable 31, and is programmable via the software to drive the rod 23 in vertical displacement in any one of a number of wave forms. While other pulses might be used, this invention has preferably utilized a relatively short term square wave pulse. That is, the actuator rod 23 moves vertically upward at the leading edge of the pulse, remains stationary in the upward position for the duration of the pulse, and then moves vertically downward to its original position at the trailing edge of the pulse. As mentioned previously, the data acquisition software for the controller 15 enables the operator to select the amount of vertical displacement, the rate of vertical displacement and the duration of the pulse. The preferable pulse duration is about five seconds and the preferable actuator rod 23 displacement rate is preferably about 100 in/min, or 1.6 in/sec, which provides a shear rate of 500 $S^{-1}$. Slower displacement rates could be used if slower shear rates are desired. In a typical test, the amount of vertical displacement at each edge of the square wave pulse was approximately ¼", although the MTS test unit 15 is capable of providing up to 20" of vertical displacement. The pulses are preferably applied in succession until the foaming polymer 18 solidifies. The elapsed time between successive pulses is also selectable, and preferably about 5 seconds.

In selecting the elapsed time between successive pulses, the operator must be careful to ensure that the rheometer 10 operates under gap loaded conditions. A gap loaded device is one in which the shear wavelength is much larger than the distance between the shearing and detecting surfaces. Gap loaded rheometers are usually used for high viscosity materials. A surface loaded apparatus, on the other hand, is one in which the amplitude of the shear wave dissipates to zero before encountering the boundary wall. In order to ensure gap loaded conditions, the ratio of the shear wavelength to the gap width must be much greater than one.

For a viscous material the planar shear wavelength is given by $$\lambda_s = \sqrt{2\pi\eta_s/fp} \qquad \text{Equation (6)}$$

where $\lambda_s$ is the shear wavelength, $\eta_s$ is the viscosity of the fluid medium, f is the frequency of oscillation, and $p$ is the density of the medium. Assuming a density of 1 g/cm$^3$, a viscosity of 10 P, and a frequency of 0.2 Hz (5 seconds), Equation 6 gives a shear wavelength of 6.98 inches.

The gap width 32 for this rheometer 10 is shown in FIG. 4. For the jacket 12 and shear plate 14 described above, the gap width 32 is just under 2" on either side of the shear plate 14. Thus, the rheometer 10 has a maximum gap between the wall of the rheometer jacket and the shearing plate of 2 inches. The rheometer 10 will be heavily gap loaded for viscosities of 100 P and above. It is important to note that as the foaming reaction progresses, the viscosity rises and the assumption of gap loading becomes increasingly valid.

For the purposes of this invention, under gap loaded conditions, the strain field in the foam rheometer 10 is assumed to be linear, and can be expressed as:

$$\gamma\, yx = \Delta x/d \qquad \text{Equation (7)}$$

where $\Delta x$ is the displacement of the plate, and d is the gap width. Based upon this assumption, if $\delta t$ is the duration of the square wave strain pulse, then Equation (1) can be rewritten as:

$$\int_0^{\delta t} \tau\, yx(t)dt = G_e \frac{\Delta x}{a} \delta t + \frac{\Delta x}{a} \eta_o \qquad \text{Equation (8)}$$

By substituting $\Delta x/d$ from Equation 7 into Equations 4 and 5, and by computing the total integrated stress response on the left side of each of these equations, the equilibrium modulus and the zero shear viscosity can be calculated.

Total integrated stress is computed, or measured, by sensing the shear forces imparted upon the shear plate 14 by the foaming polymer during each pulse and monitoring the surface area of the shear plate 14 that is in contact with the foaming polymer during the pulse. For a selectable number of discrete data acquisition points during each pulse, simultaneously occurring sensed force values and monitored height values are matched to obtain a number of discrete stress values. By using the trapezoidal rule, these discrete stress values are used to compute the total integrated stress response of the foaming polymer to the square wave.

The controller 16 enables the operator to select the number of discrete data acquisition points. A typical rate is about 20 test points per second, but the controller 16 is capable of performing as many as 200 points per second. At each acquisition point, the load cell 17 senses the shear force imparted upon the shear plate 14 by the foaming polymer 18 that is present within the jacket 12. The sensed force is conveyed to the controller 16 over cable 31, converted to a digital signal, and stored with the corresponding data acquisition point.

The surface area of the shear plate 14 that is immersed in the foaming polymer 18 is monitored by a video recorder, or by video monitoring means, shown in FIG. 1. Video monitoring means comprises a video camera 38 directed at the jacket 12 and operatively connected to a video recorder 39. Preferably, a ruler 40 is demarcated on the transparent face plate 19 of the jacket 12 to facilitate accurate monitoring. An RCA CC015 video camera in conjunction with an RCA VGP170 video cassette recorder has proved suitable for the purposes of this invention, providing resolution of foam height to within 1/32 of an inch. Because the width of shear plate 14 is known, the vertical distance between bottom edge 30 of the plate 14 and the bottom of the jacket 12 is known, i.e., the selectable displacement distance, and the speed of the videotaping is known, the surface area of the shear plate 14 that is immersed in the foaming polymer 18 can be readily computed for any point in time during the pulse.

By rerunning the tape, the monitored height values for each data acquisition point can be obtained. The sensed shear force values stored in the controller 16 can be matched with the simultaneously occurring surface area values for calculation of rheological properties. For example, the data can be input into a computer 43 such as an IBM PC-AT for analysis using data reduction routines written in RS1/RPL programming language. This programming language is a product of BBN Corporation of Cambridge, Mass. The data analysis routines calculate the stress from the measured force and height of the foam for each data acquisition point during a pulse, and then calculate the base line and perform the integration of the stress response for each pulse by using the trapezoidal rule. From the total integrated stress response for each pulse, the equilibrium modulus and the zero shear viscosity are calculated.

Figure 11:
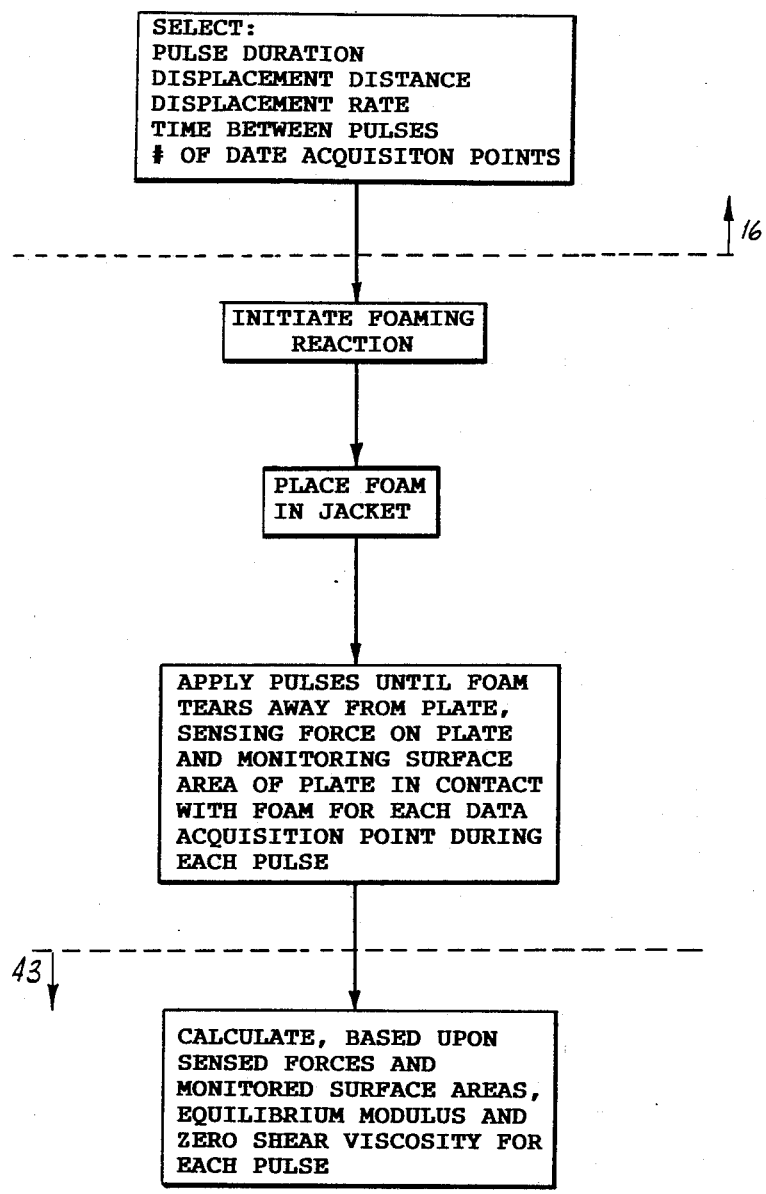
FIG. 11 is a flow chart depicting a sequence of operation using the foam pulse rheometer of this invention.

By applying successive strain pulses, until the foam tears away from the plate, and by calculating the equilibrium modulus and the zero shear viscosity for each pulse, these properties can be plotted or studied to show the evolution of the material over the course of the foaming reaction. FIG. 11 shows a sequence of operation for performing rheological testing in accordance with the invention. With respect to the initiation of foaming, it is noted that while these materials can be caused to foam by any one of a number of different methods, for the purpose of this invention the foaming reaction is initiated internally by adding a blowing agent to the polymeric starting material. While various blowing agents may be employed, depending upon the particular polymeric starting material, foaming of isocyanate materials is initiated by adding water, which causes the internal production of carbon dioxide to form the foam.

The rheometer was initially used to measure the viscosities of three high molecular weight polyols. For these experiments, the jacket 12 was altered to provide a gap width of 0.5 inches. The measurements were carried out at room temperature, using 100 points/s as the data acquisition rate. The strain used in these studies was 10% and the results are tabulated in Table I, which also shows, for comparison purposes, measured reference values obtained with a Rheometer DMS using a cone and cup fixture.

TABLE I

ZERO SHEAR VISCOSITIES OF THREE POLYOLS

| Run Number | Zero Shear Viscosity (P) (Poise) Polyol # | | |
|---|---|---|---|
| | 1 | 2 | 3 |
| 1 | 14 | 162 | 1393 |
| 2 | 8 | 153 | 1486 |
| 3 | 8 | 197 | 1441 |
| 4 | 3 | 106 | 1399 |
| 5 | 22 | 162 | 1408 |
| 6 | 8 | 116 | 1382 |
| 7 | 22 | 135 | 1377 |
| 8 | 26 | 120 | 1247 |
| 9 | 11 | 126 | 1265 |
| 10 | 7 | 117 | 1226 |
| $\lambda_s/d$ | 13 | 54 | 164 |
| mean (P) | 13 | 139 | 1362 |
| sd (P) | 8 | 28 | 87 |
| rsd (%) | 60 | 20 | 6 |
| ref (P) | 9 | 150 | 1400 |

The low viscosity polyol produced a signal that was barely discernible above the scatter in the baseline. Literature authored by Schrag and published in the *Journal of Applied Physics* (1964) 35,144 and (1965) 36, 196 has shown that true gap loaded conditions are not met until the ratio of the shear wavelength to the gap width is equal to or greater than 80. For the lowest viscosity polyol, the assumption of a linear strain field is probably not valid. The measured viscosity is of the correct order of magnitude, but scatters severely, and is only within ±40% of the reference value. For the medium viscosity polyol, for which the conditions of gap loading set forth by Schrag are close to being met, the assumption of a linear strain field is probably a good one. The precision of the rheometer for this viscosity is ±20% at one sigma, and the accuracy of the measurements is within ±8%. For the highest viscosity polyol, the conditions of gap loading are met, and the assumption of a linear strain field is an excellent one. The precision of the device for this viscosity is ±6% at one sigma and the absolute agreement with literature values is well within ±3%.

Figure 5:
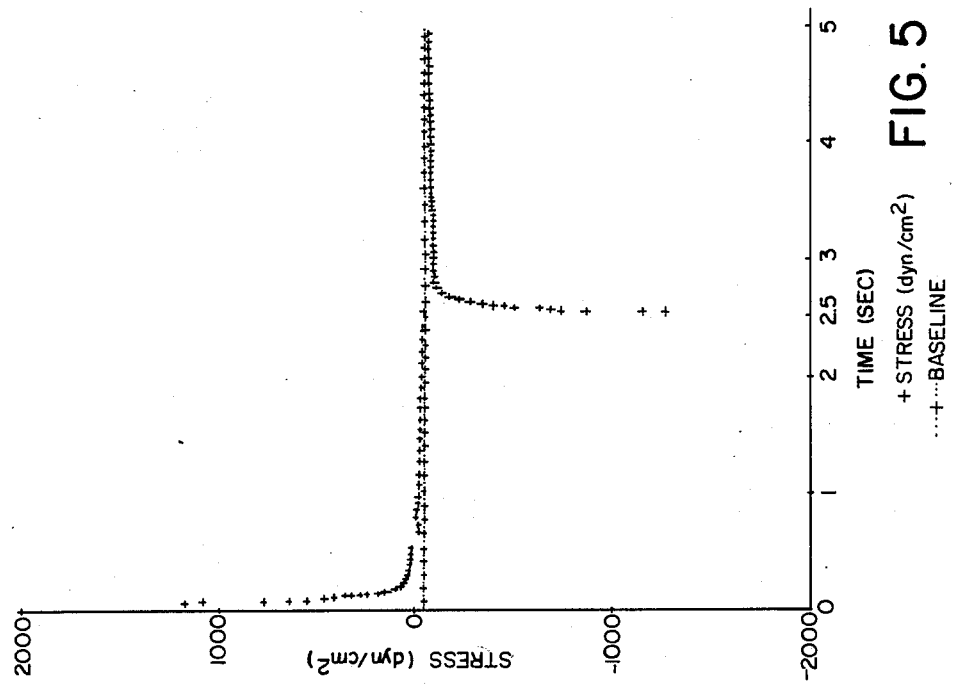
FIG. 5 is a plot of the stress response versus time during the application of one square wave strain pulse of 2.5 seconds duration for a high viscosity polyol (1400P) at room temperature and 10% strain that was obtained with the foam pulse rheometer of this invention.

FIG. 5 shows a typical stress response obtained with the high viscosity polyol in response to a 10% square wave strain pulse with a duration of 5 seconds. The two stress peaks are due to the initial imposition of the strain, positive response, and the return to an unstrained state. The stress decays rapidly to zero after the strain is applied indicating that the material doe not possess an equilibrium modulus. If it did, the stress would be expected to decay to some nonzero value until the strain was removed. The higher the equilibrium modulus, the higher the final stress state should be.

Figure 6:
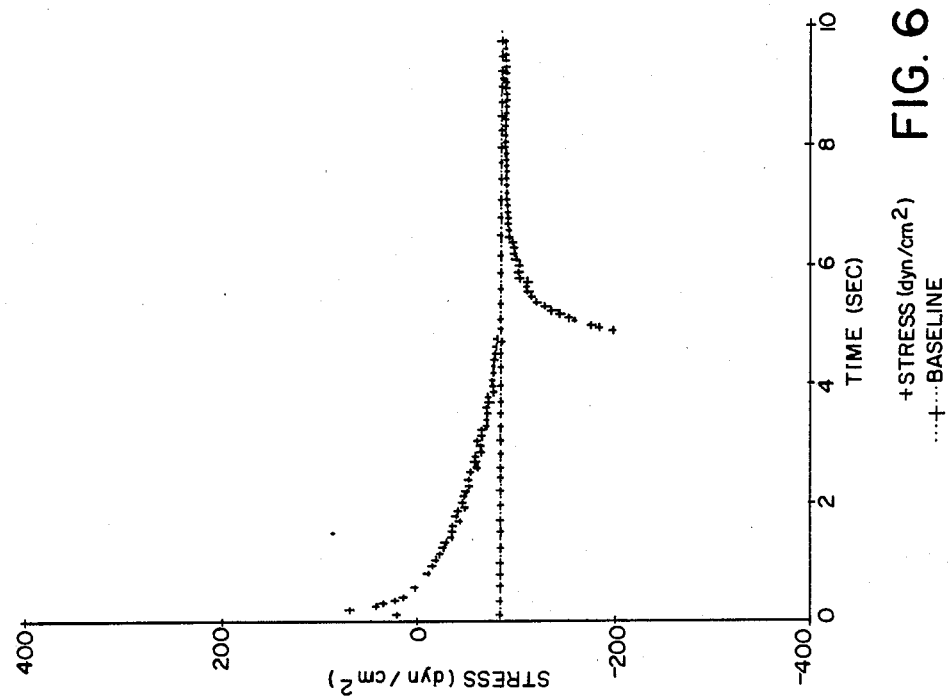
FIG. 6 is a plot of stress response versus time for a free rise polyurethane foam during the application of one square wave strain pulse 50 seconds into the reaction at room temperature and 10% strain.
Figure 8:
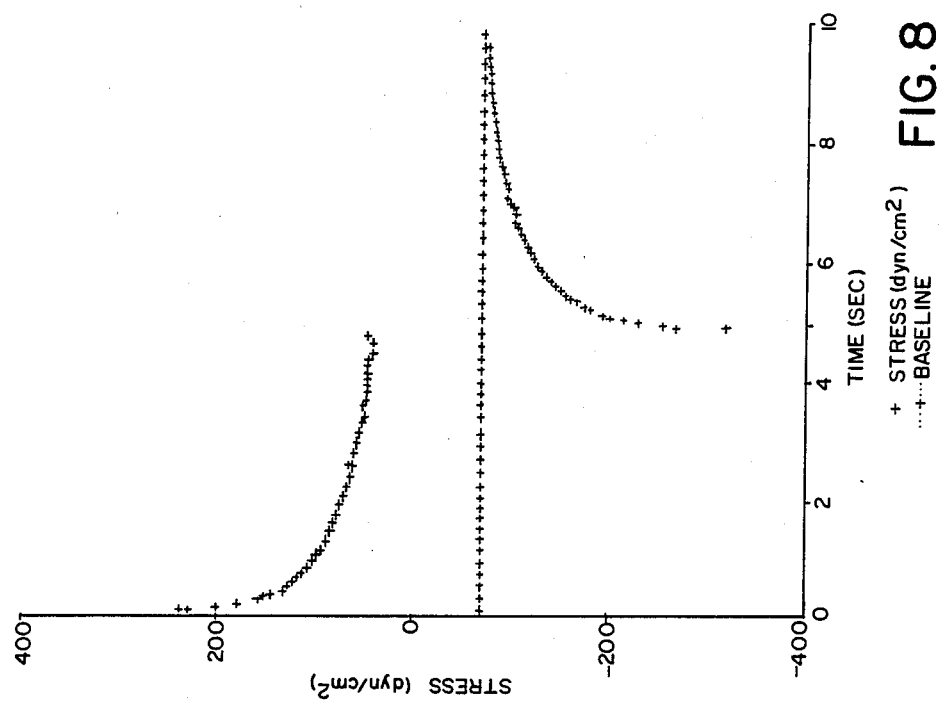
FIG. 8 is a plot similar to FIG. 6 for the same free rise foam during the application of one square wave strain pulse 190 seconds into the reaction.
Figure 7:
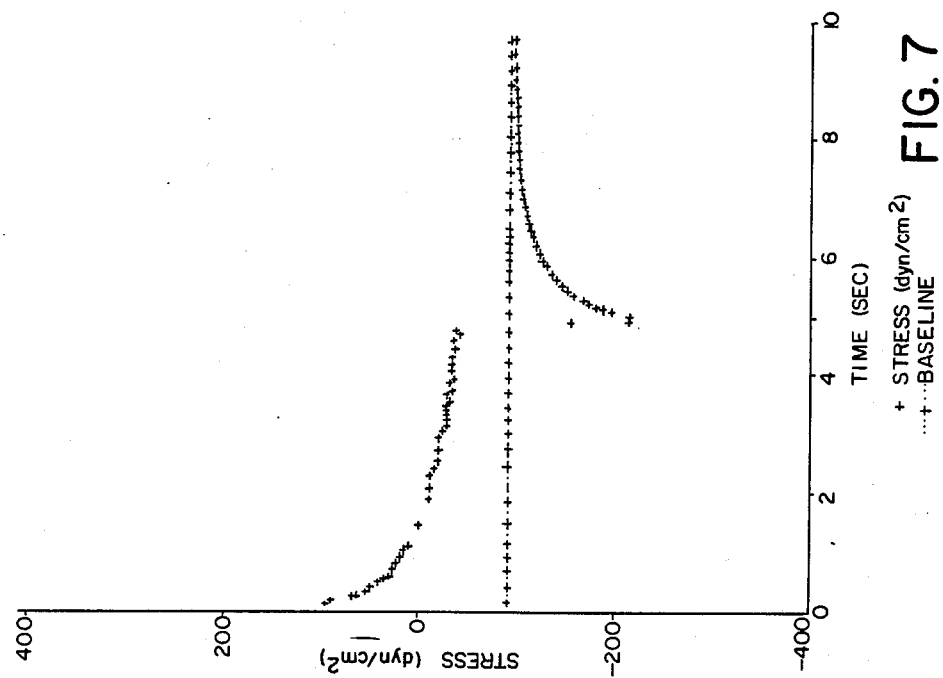
FIG. 7 is a plot similar to FIG. 6 for the same free rise foam during the application of one square wave strain pulse 90 seconds into the reaction.

The rheological properties of two free rise polyurethane foams were examined with the rheometer 10 of this invention. The experiments were conducted at room temperature using 10% strain. FIG. 6 shows the stress response curve for a pulse ending 50 seconds into the reaction. The curve resembles that of the high viscosity polyol, i.e., the response is that of a viscous or viscoelastic liquid. FIG. 7 shows the stress response for the same urethane foam 90 seconds into the reaction. The stress does not decay to zero after the imposition of the strain. This indicates that the network-like structure of the foam has now formed to a sufficient degree to possess an equilibrium modulus. FIG. 8 shows the stress response for the same urethane foam 200 seconds into the reaction. The stress plateaus at a higher level than it did at 90 seconds. This means that the equilibrium modulus is growing with time, indicating that the network structure of the foam is also growing with time.

FIG. 9 shows a plot of the equilibrium modulus versus time for two replicate runs on the same free rising polyurethane foam. The data show the onset of the modulus 50 seconds after the start of the reaction. The modulus continues to build throughout the course of the experiment. Both sets of data show the same general characteristics and agree with one another with ±15%. After the foam becomes fairly solid (after the foaming process is finished), it tears away from the shear plate 14 and subsequent measurements of the modulus are not possible.

FIG. 10 shows a plot of the zero shear viscosity versus time for the two replicate polyurethane runs discussed above. After the first twenty seconds into the reaction, the viscosity of the foam has risen to around 100 P. Past this point the apparatus is gap loaded and the accuracy of the measurements should be better than ±10%.

Initial evaluation of the rheometer 10 was performed using three polyol samples with varying viscosities. The zero shear viscosities were measured on a Rheometrics DMS and compared with the values obtained from the pulse rheometer 10. The lowest viscosity polyol produced a stress that was barely discernible above the baseline noise. However, the value obtained for the viscosity still was within ±40% of the value measured with the DMS. The two higher viscosity polyols produced more manageable signals. The precision of the measurements for the higher viscosity sample was within ±6% at one sigma and the absolute agreement with literature values was within ±3%.

Two free rise polyurethane foams were also examined with the described rheometer 10. The viscosity rose rapidly from a few poise up to nearly 5000 P in under 200 seconds. The conditions for gap loading were reached with this system in the first 10 to 20 seconds of the reaction. The modulus appeared 50 seconds into the reaction, indicating that the network structure had formed to some degree. The modulus continued to grow throughout the course of the experiment, reaching a value of just under 550 dyn/cm² at 200 seconds. Both sets of data on the two foams agreed with one another to better than ±15%.

In conclusion, the pulse rheometer 10 of this invention that has been developed in the laboratory has proven capable of providing reproducible values for the equilibrium modulus and zero shear viscosity of a cellular polymer during the foaming process. This device is capable of providing a value for the zero shear viscosity with a precision of better than ±6% at one sigma provided the conditions for gap loading are met. It is believed that this device will yield valuable insight into the rheological properties of foaming cellular polymers and further aid other experimenters in this field.

It is to be understood that neither one of the two computer program listings included in this specification is critical to the invention. While these programs provide a particular preferred sequence of operating instructions, the end result could be carried out in any number of other sequences.

TABLE II

Copyright 1989 David H. Bank

```
LIST

PULSE    7-Mar-89   MTS 773 MU BASIC V02.08

10 REM PULSE VERSION 1.0 WRITTEN BY DAVE BANK
20 DIM VA1(500,2),VA2(500,2)
30 CKTIME(1,5.00000E-03)
40 S=0 \ L=0 \ S3=0 \ S4=0 \ L4=0 \ T=0 \ T1=0 \ T2=0 \ T6=0 \ T7=0 \ T8=
50 M1=0 \ M2=0 \ L=0 \ S=0 \ S1=0 \ S2=0 \ W3=0
60 B3=0 \ B4=0 \ H=0 \ K=0
70 ADSTOP \ FGSTOP \ ADREMOVE(1,2,3)
80 CLRTXWIN
90 PRINT CHR$(27)&'#3'&'DISPLACEMENT PULSE PROGRAM'
100 PRINT CHR$(27)&'#4'&'DISPLACEMENT PULSE PROGRAM'
110 PRINT \ PRINT
120 PRINT CHR$(7)
130 PRINT 'PROGRAM DISCRIPTION: PULSE VERSION 1.0 , WRITTEN BY DAVE BANK'
140 PRINT \ PRINT
150 PRINT 'THIS PROGRAM WAS DEVELOPED FOR APPLICATION OF STROKE CONTROL'
160 PRINT 'PULSE TYPE DEFORMATION TO SAMPLES.  STRESS RELAXATION DATA IS'
170 PRINT 'ACQUIRED DURING THE COMPRESSIVE AND TENSION PORTION OF EACH '
180 PRINT 'PULSE.'
190 FOR I=1 TO 4 \ PRINT \ NEXT I
200 PRINT 'ENTER (C) TO CONTINUE, OR (M) TO RETURN TO THE MENU: ';
210 INPUT #0,Y$ \ IF Y$='C' THEN 220 \ TKCHAIN 'MENU'
220 CLRTXWIN
230 PRINT CHR$(27)&'#3'&'DISPLACEMENT PULSE SETUP MENU'
240 PRINT CHR$(27)&'#4'&'DISPLACEMENT PULSE SETUP MENU'
250 PRINT CHR$(7)
260 PRINT 'ENTER THE FLOPPY DISK DRIVE (DY1:/DY0:): '; \ INPUT #0,O$
270 PRINT CHR$(7)
280 PRINT 'ENTER THE PRIMARY DATA FILE NAME (5 CHAR OR LESS): '; \ INPUT #
290 PRINT CHR$(7)
300 PRINT 'ENTER THE SECONDARY DATA FILE NAME(5 CHAR OR LESS): ';
305 INPUT #0,G$
310 PRINT CHR$(7)
320 PRINT 'ENTER THE NUMBER OF PULSES FOR THIS EXPERIMENT: '; \ INPUT #0,
330 PRINT CHR$(7)
340 PRINT 'ENTER THE STROKE RANGE (IN): '; \ INPUT #0,S
350 PRINT CHR$(7)
360 PRINT 'ENTER THE LOAD RANGE (LBS): '; \ INPUT #0,L
370 PRINT CHR$(7)
380 PRINT 'ENTER THE DISPLACEMENT RATE (IN/MIN): '; \ INPUT #0,R
390 R=R/60
400 PRINT CHR$(7)
410 PRINT 'ENTER THE DESIRED AMOUNT OF ACTUATOR DISPLACEMENT (IN): ';
420 INPUT #0,S1
430 S2=S1/S
440 T=S2/R
450 S2=-S2
460 PRINT CHR$(7)
470 PRINT 'ENTER THE PRIMARY PULSE LENGTH (SEC): '; \ INPUT #0,T8
480 PRINT CHR$(7)
490 PRINT 'ENTER THE SECONDARY PULSE LENGTH (SEC):  '; \ INPUT #0,T7
500 CLRTXWIN
510 PRINT CHR$(27)&'#3'&'DATA ACQUISITION INFORMATION'
520 PRINT CHR$(27)&'#4'&'DATA ACQUISITION INFORMATION'
530 FOR I=1 TO 4 \ PRINT \ NEXT I \ PRINT CHR$(7)
540 PRINT 'ENTER THE DATA ACQUISITION SPEED FOR THE PRIMARY PULSE (PTS/SEC
```

```
550 INPUT #0,T9 \ T3=(1/5.00000E-03)*(1/T9)
560 PRINT CHR$(7)
570 PRINT 'ENTER THE DATA ACQUISITION SPEED FOR THE SECONDARY PULSE (PT/S)
580 INPUT #0,T6 \ T4=(1/5.00000E-03)*(1/T6)
590 CLRTXWIN
600 PRINT CHR$(27)&'#3'&'TEST PARAMETER MENU'
610 PRINT CHR$(27)&'#4'&'TEST PARAMETER MENU'
620 PRINT \ PRINT
630 PRINT 'DISK DRIVE                   : 'O$
640 PRINT 'DATA FILE NAME               : 'D$
650 PRINT 'SAMPLE DISCRIPTION           : 'M$
660 PRINT 'STROKE RANGE (in)            :'S
670 PRINT 'LOAD RANGE (lbs)             :'L
680 PRINT 'DISPLACEMENT RATE (in/min)   :'R*60
690 PRINT 'ACTUATOR DISPLACEMENT (in)   :'S1
700 PRINT 'NUMBER OF PULSES             :"H
710 PRINT 'PRIMARY PULSE WIDTH     :",T8
720 PRINT 'SECONDARY PULSE WIDTH   :",T6
730 PRINT \ PRINT
740 PRINT CHR$(7)
750 PRINT 'ARE ALL PARAMETERS CORRECT (Y/N)    : '; \ INPUT #0,Y$
760 IF Y$='N' THEN 90
770 CLRTXWIN
780 PRINT CHR$(27)&'#3'&'INSTRUMENT SETUP MENU'
790 PRINT CHR$(27)&'#4'&'INSTRUMENT SETUP MENU'
800 FOR I=1 TO 4 \ PRINT \ NEXT I
810 PRINT CHR$(7)
820 PRINT '1. CLEAR D/A' \ PRINT
830 PRINT '2. SET INTERLOCKS FOR LOAD AND STROKE' \ PRINT
840 PRINT '3. PUT THE HYDRAULICS IN LOW IN STROKE CONTROL' \ PRINT
850 PRINT '4. LOAD SAMPLE' \ PRINT
860 PRINT '5. BRING THE HYDRAULICS TO HIGH' \ PRINT
870 FOR I=1 TO 4 \ PRINT \ NEXT I
880 PRINT CHR$(7)
890 PRINT 'HIT A RETURN TO BEGIN TESTING: '; \ INPUT #0,R$
900 CLRTXWIN
910 PRINT CHR$(27)&'#3'&'    TEST IN PROGRESS'
920 PRINT CHR$(27)&'#4'&'    TEST IN PROGRESS'
930 FGREMOTE(1,3,F)
940 H=H+1 \ K=K+1 \ B4=B4+1
950 IF H<>9 THEN 970
960 H=H+1 \ K=0
970 IF K<>9 THEN 982
980 H=H+1 \ K=0
982 IF H<>90 THEN 990
984 H=H+10 \ K=0
990 ADTIMED(1,VA1,,1,T3,3) \ ADTIMED(2,VA2,,1,T4,3)
1000 ADINIT \ ADGO(1) \ ETIME
1010 FGGO \ FGIMMED(1,"RAMP", TIME T,S2)
1020 ETIME \ SLEEP(T8)
1030 ADHOLD(1) \ FGSTOP \ ADGO(2)
1040 FGIMMED(1,"RAMP", TIME T,0) \ GTIME(A,B,C)
1050 PRINT 'PULSE: "H
1060 OPEN D$+STR$(H) FOR OUTPUT AS FILE VF1, FILESIZE 20, ERROR E0
1070 F=1
1080 FOR I=1 TO VA1
1090 VF1(F)=VA1(I,0)
1100 VF1(F+1)=VA1(I,1)
1110 VF1(F+2)=VA1(I,2)
1120 F=F+3
1130 NEXT I
1140 CLOSE VF1
1150 ETIME \ GTIME(A1,B1,C1)
1160 G=(A1+B1*60+C1*3600)-(A+B*60+C*3600)
1170 IF G<T7 THEN 1150
1180 ADHOLD(2) \ ADSTOP
1190 OPEN E$+STR$(H) FOR OUTPUT AS FILE VF2, FILESIZE 20, ERROR E0
```

```
1200 F=1
1210 FOR I=1 TO VA2
1220 VF2(F)=VA2(I,0)
1230 VF2(F+1)=VA2(I,1)
1240 VF2(F+2)=VA2(I,2)
1250 F=F+3
1260 NEXT I
1270 CLOSE VF2
1280 ADREMOVE(1,2)
1290 IF H<>J THEN 940
1300 H=0 \ C=0
1310 H=H+1 \ C=C+1
1330 IF H<>9 THEN 1350
1340 H=H+1 \ C=0
1350 IF C<>9 THEN 1362
1360 H=H+1 \ C=0
1362 IF H<>90 THEN 1370
1364 H=H+10 \ C=0
1370 CLRTXWIN
1380 PRINT CHR$(27)&'#3'&'DATA DUMP TO FLOPPY'
1390 PRINT CHR$(27)&'#4'&'DATA DUMP TO FLOPPY'
1400 PRINT \ PRINT
1420 PRINT "PROCESSING DATA FOR PULSE #"H
1430 FOR I=1 TO 8 \ PRINT \ NEXT I
1440 PRINT "TIME          LOAD           STROKE"
1450 PRINT CHR$(27);"[16;r";CHR$(27);"[16;1H";
1460 OPEN D$+STR$(H) AS FILE VF1, ERROR E0
1470 F=1
1480 FOR I=1 TO 500
1490 VA1(I,0)=VF1(F)
1500 VA1(I,1)=VF1(F+1)
1510 VA1(I,2)=VF1(F+2)
1520 F=F+3
1530 NEXT I
1540 CLOSE VF1
1550 OPEN O$+D$+STR$(H)+".DSH" FOR OUTPUT AS FILE #1, FILESIZE 50, ERROR E
1560 FOR I=1 TO VA1
1570 T1=(5.00000E-03*(VA1(I,0)))
1580 L3=(L*(VA1(I,1)/32767))
1590 S3=(S*(VA1(I,2)/32767))
1600 PRINT #1,T1,L3,S3 \ PRINT T1,L3,S3
1610 NEXT I
1620 CLOSE #1
1630 OPEN E$+STR$(H) AS FILE VF2, FILESIZE 200, ERROR E0
1640 F=1
1650 FOR I=1 TO 500
1660 VA2(I,0)=VF2(F)
1670 VA2(I,1)=VF2(F+1)
1680 VA2(I,2)=VF2(F+2)
1690 F=F+3
1700 NEXT I
1710 CLOSE VF2
1720 OPEN O$+E$+STR$(H)+".DSH" FOR OUTPUT AS FILE #2, FILESIZE 50, ERROR
1730 FOR I=1 TO VA2
1740 T1=(5.00000E-03*(VA2(I,0)))
1750 L3=(L*(VA2(I,1)/32767))
1760 S3=(S*(VA2(I,2)/32767))
1770 PRINT #2,T1,L3,S3 \ PRINT T1,L3,S3
1780 NEXT I
1790 CLOSE #2
1800 IF H<>B4 THEN 1310
1810 A=0 \ C=0
1820 FOR I=1 TO B4
1830 A=A+1 \ C=C+1
1840 IF A<>9 THEN 1860
1850 A=A+1 \ C=0
1860 IF C<>9 THEN 1872
1870 A=A+1 \ C=0
```

```
1872 IF A<>90 THEN 1880
1874 A=A+10 \ C=0
1880 KILL D$+STR$(A) \ KILL E$+STR$(A)
1890 NEXT I
1900 PRINT CHR$(7)
1910 CLRTXWIN
1920 PRINT 'HIT THE RETURN KEY WHEN THE HYDRAULICS ARE DOWN: ';
1930 INPUT #0,H$
1940 IF H$<>' ' THEN 1920
1950 ADSTOP \ FGSTOP \ FGLOCAL
1960 GO TO 2350
1970 FOR I=1 TO VA1
1980 VA1(I,1)=(L*ELEVEL(VA1(I,1)))
1990 VA1(I,2)=(S*ELEVEL(VA1(I,2)))
2000 NEXT I
2010 FOR I=1 TO VA2
2020 VA2(I,1)=(L*ELEVEL(VA2(I,1)))
2030 VA2(I,2)=(S*ELEVEL(VA2(I,2)))
2040 NEXT I
2050 M=0
2060 IF M=0 THEN 2080
2070 M=1
2080 CLRTXWIN
2090 M1=T8 \ M2=L \ REM SCALING FACTORS
2100 VTMODE \ CLRTXWIN \ TEKMODE
2110 PHYL(1,0,100,11.67,95)
2120 SCALE(1,2,.01,M1,0,M2)
2130 INVEC(1)
2140 FOR I=1 TO VA1
2150 PLOT(1,VA1(I,0),VA1(I,1)) \ NEXT I
2160 FOR I=1 TO VA2
2170 PLOT(1,VA2(I,0),VA2(I,1)) \ NEXT I
2180 AXES(1,.01,0)
2190 LABEL(1,'log TIME (*sec)','LOAD (lbs)',M1,M2,1)
2200 COMM(1,M$,.1M1,M2)
2210 IF M=1 THEN 2300
2220 COMM(1,'WOULD YOU LIKE TO CHANGE THE SCALE [N]: ',.1M1,.95M2)
2230 INPUT #0,Y$ \ IF Y$=' ' THEN 2070
2240 COMM(1,'ENTER THE LOAD AXIS LIMIT: ',.1M1,.9M2)
2250 INPUT #0,M2
2260 COMM(1,'ENTER THE TIME AXIS LIMIT: ',.1M1,.85M2)
2270 INPUT #0,M1
2280 GO TO 2080
2290 REM HARD COPY OUTPUT
2300 ETIME \ SLEEP(1) \ COPY \ SLEEP(10) \ VTMODE
2310 PRINT CHR$(27)&"[?5Ii" \ REM TURN AUTO PRINT ON
2320 PRINT \ PRINT
2330 PRINT M$
2340 PRINT 'DATA FILE NAME      : 'D$
2350 PRINT 'LOAD RANGE (lbs)    :'L
2360 PRINT 'STROKE RANGE (in)   :'S
2370 PRINT 'TEST RATE (in/min)  :'R
2380 PRINT 'GAGE LENGTH (in)    :'G
2390 PRINT 'CROSS SECTIONAL AREA:'A9
2400 PRINT ' EXTENTION          :'(S1/G)*100
2410 PRINT 'TEST DURATION (sec) :'T8
2420 PRINT CHR$(12) \ REM FORM FEED
2430 PRINT CHR$(27)&"[?4i" \ REM TURN OFF AUTO PRINT
2440 TKCHAIN "MENU" LINE 10

Ready
```

TABLE III

Copyright 1989 Craig J. Carriere

```
N=GETNUMBER('ENTER THE NUMBER OF DATA FILES TO BE PROCESSED :');
ALLOCATE TABLE(ARA) N ROWS BY 5 COLUMNS;
DO N1=1 TO N;
     CALL ERASE;
        TN=CAT('ENTER THE TABLE NAME FOR PULSE #',N1,': ');
        ARA[N1,1]=GETTABLE(TN);
        TX=CAT('ENTER THE GRAPH TITLE FOR PULSE #',N1,': ');
        ARA[N1,2]=GETTEXT(TX);
     XA=CAT('ENTER THE PLATE WIDTH (IN) FOR PULSE #',N1,': ');
     ARA[N1,3]=GETNUMBER(XA);
     RR=CAT('ENTER THE FOAM RISE RATE (IN/MIN) FOR PULSE #',N1,': ');
     ARA[N1,4]=GETNUMBER(RR);
     IH=CAT('ENTER THE INITIAL FOAM HEIGHT (IN) FOR PULSE #',N1,': ');
     ARA[N1,5]=GETNUMBER(IH);
END;
DO P=1 TO N;
        TN=ARA[P,1];
        TX=ARA[P,2];
        XA=ARA[P,3];
     RR=ARA[P,4];
     IH=ARA[P,5];
     XA=XA*2.54;
     RR=RR*2.54/60;
     IH=IH*2.54;
        SN=CAT(TN,'_ST');
        DO I=2 TO LASTROW(TN);
               TN[I,1]=TN[I-1,1]+TN[I,1];
             IF TN[I,2] > 5.0 THEN
                   BEGIN;
                      TN[I,2]=0.0;
                END;
                IF TN[I,2]< -5.0 THEN
                      BEGIN;
                      TN[I,2]=0.0;
                END;
        END;
     LR = LAST ROW OF TABLE(TN);
     IF TN[LR,1] > 2*TN[LR-1,1] THEN
           BEGIN;
           DELETE ROW LR OF TABLE(TN);
        END;
        TYPE 'CREATING TABLE FOR STRESS DATA';
     COL 4 OF TABLE(TN)=(COL 2 *981*1000/2.2/((IH+RR* COL 1 )*XA*2));
     TN[0,4]='STRESS (DYN/CM2)';
        DELETE ROW 1 OF TABLE(TN);
        MAKE TABLE(SN) FROM COLS 1 TO 4 OF TABLE(TN);
/*----------GENERATE PLOT OF LOAD VS TIME------------*/
        GN=CAT(TN,'_G1');
        TYPE 'MAKING LOAD VS TIME PLOT';
        MAKE GRAPH(GN) FROM COL 1 OF TABLE(TN) VS COL 2;
        GRAPHTITLE OF GRAPH(GN)=TX;
        ORIENTATION OF Y AXIS OF GRAPH(GN)='VERTICAL';
     LABEL OF X AXIS OF GRAPH(GN)='TIME (sec)';
        LABEL OF Y AXIS OF GRAPH(GN)='LOAD (lbs)';
        SYMBOL OF CURVE 1 OF GRAPH(GN)='+';
     LOW OF X AXIS OF GRAPH(GN)='0.0';
     LINLOG OF X AXIS OF GRAPH(GN)='LIN';
        HIGH OF Y AXIS OF GRAPH(GN)='0.5';
```

```
            DISPLAY GRAPH(GN);
/*--------GENERATE PLOT OF STRESS VS TIME---------------*/
        TYPE 'MAKING STRESS VS TIME PLOT';
        GS=CAT(TN,'_G2');

MAKE GRAPH(GS) FROM COL 1 OF TABLE(SN) VS COL 4;
        GRAPHTITLE OF GRAPH(GS)=TX;
        ORIENTATION OF Y AXIS OF GRAPH(GS)='VERTICAL';
        LABEL OF X AXIS OF GRAPH(GS)='TIME (sec)';
        LABEL OF Y AXIS OF GRAPH(GS)='STRESS (dyn/cm2)';
        SYMBOL OF CURVE 1 OF GRAPH(GS)='+';
        LOW OF X AXIS OF GRAPH(GS)='0.0';
        DISPLAY GRAPH(GS) BOTTOMKEY;
END;

N=GETNUMBER('ENTER THE NUMBER OF PULSES TO BE ANALYZED :');
ALLOCATE TABLE(ARA) N ROWS BY 4 COLUMNS;
ALLOCATE TABLE(FRR) N ROWS BY 6 COLUMNS;
FRR = 'RESULTS';
DO N1=1 TO N;
        CALL ERASE;
        TU=CAT('ENTER THE TABLE NAME FOR STARTING PULSE #',N1,': ');
        ARA[N1,1]=GETTABLE(TU);
        TD=CAT('ENTER THE TABLE NAME FOR RETURN PULSE #',N1,': ');
        ARA[N1,2]=GETTABLE(TD);
        TB=CAT('ENTER THE TABLE NAME FOR THE RETURN PULSE OF THE PREVIOUS SET :');
        ARA[N1,5]=GETTABLE(TB);
        GW=CAT('ENTER THE GAP WIDTH-(IN) FOR PULSE PAIR #',N1,': ');
        ARA[N1,3]=GETNUMBER(GW);
        AD=CAT('ENTER THE ACTUATOR DISPLACEMENT (IN) FOR PULSE PAIR #',N1,': ');
        ARA[N1,4]=GETNUMBER(AD);
END;
DO P=1 TO N;
        TU=ARA[P,1];
        TD=ARA[P,2];
        GW=ARA[P,3];
        GW=GW*2.54;
        AD=ARA[P,4];
        AD=AD*2.54;
        TB=ARA[P,5];
/* CALCULATING THE BASELINE FOR THE PULSE ANALYSIS*/
        TYPE ' ';
        TYPE'CALCULATING BASELINE FOR STRESS DATA';
        Z = LAST ROW OF TABLE(TB);
        TIME = TB[Z,1];
        BL=CAT(TU,'_BL');
        BL[0,1]='TIME (SEC)';
        BL[0,2]='STRESS (DYN/CM2)';
        BL[0,3]='TIME (SEC)';
        BL[0,4]='STRESS (DYN/CM2)';
        DO I=1 TO 5;
            BL[I,1]=TB[Z-I,1];
            BL[I,2]=TB[Z-I,4];
        END;
        Z = LAST ROW OF TABLE(TU);
        DO I=1 TO 5;
            BL[I,3]=TD[Z-I,1] + TIME;
            BL[I,4]=TD[Z-I,4];
        END;
        BL[0,5] = 'MEAN TIME';
        BL[0,6] = 'MEAN STRESS';
        BL[1,5] = 0.0;
        BL[2,5] = MEAN OF COL 3 OF TABLE(BL);
        BL[1,6] = MEAN OF COL 2 OF TABLE(BL);
        BL[2,6] = MEAN OF COL 4 OF TABLE(BL);
```

```
      SLOPE=(BL[2,6]-BL[1,6])/(BL[2,5]-BL[1,5]);
      INTER=BL[1,6]-SLOPE*BL[1,5];
/* CALCULATING THE STRESS INTEGRALS FOR THE PULSE SEQUENCE */
      SN=CAT(TU,'_IS');
      TYPE ' ';
      TYPE 'CREATING TABLE FOR STRESS INTEGRAL DATA';
      MAKE TABLE(SN) FROM COLS 1 TO 4 OF TABLE(TU);
      SN[0,5] = 'CORR STRESS';
      SN[0,6]='STRESS INTEGRAL';

SN[1,5]=SN[1,4]-(SLOPE*SN[1,1]+INTER);
      N= LAST ROW OF TABLE(SN);
      DO I=2 TO N-1;
          SN[I,5]=(SN[I,4]-(SLOPE*SN[I,1]+INTER))*2;
      END;
      SN[N,5]=SN[N,4]-(SLOPE*SN[N,1]+INTER);
      SI1= SUM OF COL 5 OF TABLE(SN);
      SI1=(SI1/(2*N))*(SN[N,1]-SN[1,1]);
      SN[1,6]=SI1;
      SD=CAT(TD,'_IS');
      MAKE TABLE(SD) FROM COLS 1 TO 4 OF TABLE(TD);
      SD[0,5] = 'STRESS*TIME';
      SD[0,6] = 'STRESS INTEGRAL';
      N2= LAST ROW OF TABLE(SD);
      SD[1,5]=SD[1,4]-(SLOPE*SD[1,1]+INTER);
      DO I=2 TO N2-1;
          SD[I,5]=(SD[I,4]-(SLOPE*SD[I,1]+INTER))*2;
      END;
      SD[N2,5]=SD[N2,4]-(SLOPE*SD[N2,1]+INTER);
      SI2= SUM OF COL 5 OF TABLE(SD);
      SI2=(SI2/(2*N2))*(SD[N2,1]-SD[1,1]);
      SD[1,6]=SI2;
      SI = SN[1,6]+SD[1,6];
      TP1 = SN[N,1];
      TP2 = SD[N2,1];
      TP = TP1 + TP2;
      GA=SI*GW/(AD*TP);
      ETA=GW*SI1/AD-GA*TP1;
      TYPE ' ';
      TYPE NOCR 'EQUILIBRIUM MODULUS (DYN/CM2): ',INTEGER(GA+0.5);
      TYPE ' ';
      TYPE NOCR 'ZERO SHEAR VISCOSITY (P): ',INTEGER(ETA+0.5);
      TYPE ' ';
      SN[0,7] = 'Ge (DYN/CM2)';
      SN[0,8] = 'ETA (P)';
      SN[1,7]=GA;
      SN[1,8]=ETA;
      SN[0,9] = 'BASELINE';
      SD[0,7] = 'BASELINE';
      COL 7 OF TABLE(SD) = SLOPE * ( COL 1 + TP1) + INTER;
      COL 9 OF TABLE(SN) = SLOPE * COL 1 + INTER;
/*-------GENERATE TABLE OF FINAL RESULTS-------------------*/
      FRR[0,1]= 'TIME (sec)';
      FRR[0,2]= 'PULSE#';
      FRR[0,3]= 'Ge (dyn/cm2)';
      FRR[0,4]= 'ETA (P)';
      FRR[0,5]= 'GAP WIDTH (in)';
      FRR[0,6]= 'DISP (in)';
      FRR[P,1]= P*TP;
      FRR[P,2]= P;
      FRR[P,3]= GA;
      FRR[P,4]= ETA;
      FRR[P,5]= GW/2.54;
      FRR[P,6]= AD/2.54;
/*------GENERATE PLOT OF STRESS VS TIME WITH BASELINE----*/
      GS=CAT(TU,'_G2');
```

```
        TYPE ' ';
        TYPE NOCR 'ADDING BASELINE TO STRESS VS TIME PLOT ',GS;
        TYPE' ';
        ADD CURVE TO GRAPH(GS) FROM COL 9 OF TABLE(SN);
        SET CONNECTED OF CURVE 2 OF GRAPH(GS) TO 'YES';
        SYMBOL OF CURVE 2 OF GRAPH(GS)='+';
        LINE OF CURVE 2 OF GRAPH(GS)='DOT';
        COLOR OF CURVE 2 OF GRAPH(GS)='GREEN';
        DISPLAY GRAPH(GS);

GN=CAT(TD,'_G2');
        TYPE NOCR 'ADDING BASELINE TO STRESS VS TIME PLOT ',GN;
        TYPE ' ';
        ADD CURVE TO GRAPH(GN) FROM COL 7 OF TABLE(SD);
        SET CONNECTED OF CURVE 2 OF GRAPH(GN) TO 'YES';
        SYMBOL OF CURVE 2 OF GRAPH(GN)='+';
        LINE OF CURVE 2 OF GRAPH(GN)='DOT';
        COLOR OF CURVE 2 OF GRAPH(GN)='GREEN';
        DISPLAY GRAPH(GN);
/*-------GENERATE COMPOSITE STRESS VS TIME PLOT----------*/
        TYPE 'MAKING COMPOSITE STRESS VERSUS TIME PLOT';
        SC=CAT(TU,'_COMP');
        DO I=1 TO N;
             SC[I,1]=SN[I,1];
             SC[I,2]=SN[I,4];
             SC[I,3]=SN[I,9];
        END;
        DO I=1 TO N2;
             SC[I+N,1]=SD[I,1] + SN[N,1];
             SC[I+N,2]=SD[I,4];
             SC[I+N,3]=SD[I,7];
        END;
        GC=CAT(TU,'_COMP');
        MAKE GRAPH(GC) FROM COL 1 OF TABLE(SC) VS COL 2;
        GRAPHTITLE OF GRAPH(GC)=GC;
        ORIENTATION OF Y AXIS OF GRAPH(GC)='VERTICAL';
        LABEL OF X AXIS OF GRAPH(GC)='TIME (sec)';
        LABEL OF Y AXIS OF GRAPH(GC)='STRESS (dyn/cm2)';
        SYMBOL OF CURVE 1 OF GRAPH(GC)='+';
        LABEL OF CURVE 1 OF GRAPH(GC)='STRESS (dyn/cm2)';
        ADD CURVE TO GRAPH(GC) FROM COL 3 OF TABLE(SC);
        SET CONNECTED OF CURVE 2 OF GRAPH(GC) TO 'YES';
        SYMBOL OF CURVE 2 OF GRAPH(GC) ='+';
        LINE OF CURVE 2 OF GRAPH(GC) ='DOT';
        COLOR OF CURVE 2 OF GRAPH(GC) = 'GREEN';
        LABEL OF CURVE 2 OF GRAPH(GC) = 'BASELINE';
        DISPLAY GRAPH(GC) BOTTOMKEY;
        DELETE TABLE(SC);
        DELETE TABLE(BL);
END;
```

While a foam pulse rheometer in accordance with the invention has been described, it is to be understood that that the invention is not limited thereby and that in light of the present disclosure, various other alternative embodiments will be apparent to one of ordinary skill in the art without departing from the scope of the invention. Accordingly, applicant intends to be bound only by the following claims.

We claim:

1. A rheometer system comprising:
a jacket for containing a foaming material;
a shear plate extending at least partially into said jacket;
means for applying a strain pulse to said jacket;
measuring means operatively associated with said shear plate for measuring the total integrated stress response to said strain pulse of a foaming material contacting said plate when in said jacket.

2. The rheometer of claim 1 wherein said jacket is transparent and said measuring means further comprises:
means for sensing the shear force imparted upon said immersed shear plate by said foaming material during application of said strain pulse; and
means for monitoring the surface area of said shear plate immersed in said foaming material during said strain pulse, for providing surface area values which can be used in conjunction with sensed shear forces to compute said total integrated stress response.

3. The rheometer of claim 2 wherein said sensing means is a load cell operatively connected to said shear plate.

4. The rheometer of claim 2 wherein said surface area monitoring means further comprises:
a video recording means directed at said jacket; and
a ruler mounted to said jacket, said recording means visually recording the height of the foaming material in the jacket during the strain pulse.

5. The rheometer of claim 1, and further comprising:
means for calculating, based upon said measured integrated stress response, the equilibrium modulus and the zero shear viscosity of said foaming material during said strain pulse.

6. The rheometer of claim 2 wherein said transparent jacket has a removable face plate.

7. The rheometer of claim 4 wherein said transparent jacket has a removable face plate, and said ruler is demarcated on said removable face plate.

8. The rheometer of claim 1 wherein said material is a foaming cellular polymer, and said jacket has two parallel side walls, with said shear plate situated halfway between, and parallel with, said side walls, and the distance from each of said side walls to said shear plate assures gap loaded operation.

9. The rheometer of claim 1 wherein said shear plate has a sharpened bottom edge, thereby to minimize compressive loading of said material during said strain pulse.

10. The rheometer of claim 1 wherein said applying means applies a square wave strain pulse.

11. A rheometer system comprising:
a transparent jacket for containing a foaming polymer;
a shear plate extending at least partially into said jacket;
means for applying a strain pulse to said jacket;
a load cell operatively connected to said shear plate to sense, during said strain pulse, the shear force imparted upon said shear plate by a foaming polymer contained in said jacket; and
video recording means for monitoring the surface area of said shear plate immersed in said foaming polymer during said strain pulse; and
means for calculating, based upon said sensed force and said monitored surface area, the equilibrium modulus and the zero shear viscosity of said foaming polymer for said strain pulse.

12. The rheometer of claim 11 wherein said applying means applies successive strain pulses to said jacket until said foaming polymer tears away from said plate, and said rheometer calculates an equilibrium modulus and a zero shear viscosity for each said applied strain pulse.

13. The rheometer of claim 12 wherein each said strain pulse is a square wave of five seconds duration.

14. A method for determining the equilibrium modulus and the zero shear viscosity of a foaming polymer comprising the steps of:
introducing a foaming polymer into a jacket;
applying a strain pulse to said jacket;
measuring the total integrated stress response of said foaming polymer to said strain pulse; and
calculating, based upon said measured total integrated stress response, the equilibrium modulus and the zero shear viscosity of said foaming polymer for said strain pulse.

15. The method of claim 14 wherein said jacket is transparent and said measuring step further comprises the steps of:
sensing the shear force imparted upon a shear plate immersed within said foaming polymer during said strain input;
monitoring the surface area of said shear plate that is immersed in said foaming polymer during said sensing.

16. The method of claim 14 wherein successive said strain pulses are applied, and said measuring and said calculating steps are performed for each of said successively applied strain pulses.

17. The method of claim 16 wherein said strain pulses are square waves.

18. The method of claim 17 wherein the rate of application of said square waves is selectable.

19. The method of claim 18 wherein said selectable rate is about 1.6 inches per second.

20. The method of claim 17 wherein the duration of said square waves is selectable.

21. The method of claim 20 wherein said duration is about five seconds.

22. The method of claim 17 wherein the elapsed time between successive square wave pulses is selectable.

23. The method of claim 22 wherein said elapsed time is approximately five seconds.

24. The method of claim 22 wherein said elapsed time between successive pulses is chosen to ensure gap loaded conditions for said foaming polymer.

25. The method of claim 14 and further comprising the step of:
matching simultaneously occurring sensed force values and monitored height values for each of a discrete number of data acquisition points during said strain pulse.

26. The method of claim 25 wherein said discrete number is selectable.

27. The method of claim 26 wherein said discrete number is 20 points per second.

* * * * *

UNITED STATES PATENT AND TRADEMARK OFFICE
CERTIFICATE OF CORRECTION

PATENT NO. : 4,905,504

DATED : Mar. 6, 1990                                        Page 1 of 3

INVENTOR(S) : Craig J. Carriere, David H. Bank, Christopher P. Christenson

It is certified that error appears in the above-identified patent and that said Letters Patent is hereby corrected as shown below:

Title page:

Under the heading "References Cited" the following references should be listed. (See attached sheets.)

UNITED STATES PATENT AND TRADEMARK OFFICE
CERTIFICATE OF CORRECTION

PATENT NO. : 4,905,504

DATED : Mar. 6, 1990

INVENTOR(S) : Craig J. Carriere, David H. Bank, Christopher P. Christenson

It is certified that error appears in the above-identified patent and that said Letters Patent is hereby corrected as shown below:

Under the heading "References Cited" list the following references cited in PTO Form 1449 included in the Information Disclosure Statement dated October 6, 1989:

U.S. PATENT DOCUMENTS

| EXAMINER INITIAL | DOCUMENT NUMBER | DATE | NAME | CLASS | SUBCLASS | FILING DATE IF APPROPRIATE |
|---|---|---|---|---|---|---|
| AA | 3,636,753 | 1/15/72 | Thiele et al. | 73 | 59 | |
| AB | 3,741,002 | 6/26/73 | Simons | 73 | 64.1 | |
| AC | 3,803,903 | 4/16/74 | Lin | 73 | 59 | |
| AD | 4,403,502 | 9/13/83 | Lindt | 73 | 55 | |
| AE | 4,464,928 | 8/14/84 | Dealy | 73 | 54 | |
| AF | 4,559,811 | 12/24/85 | Higgs et al. | 73 | 59 | |
| AG | 4,571,989 | 2/15/86 | Dealy | 73 | 60 | |
| AH | 4,559,812 | 12/24/85 | Kitchen | 73 | 59 | |
| AI | 4,566,324 | 1/28/86 | Vinogradov et al. | 73 | 60 | |
| AJ | 4,633,708 | 1/6/87 | Blommaert | 73 | 59 | |
| AK | 4,643,020 | 2/17/87 | Heinz | 73 | 59 | |

UNITED STATES PATENT AND TRADEMARK OFFICE
CERTIFICATE OF CORRECTION

PATENT NO. : 4,905,504

DATED : Mar. 6, 1990

INVENTOR(S) : Craig J. Carriere, David H. Bank, Christopher P. Christenson

It is certified that error appears in the above-identified patent and that said Letters Patent is hereby corrected as shown below:

| | FOREIGN PATENT DOCUMENTS | | | | | | |
|---|---|---|---|---|---|---|---|
| | DOCUMENT NUMBER | DATE | COUNTRY | CLASS | SUBCLASS | TRANSLATION YES | NO |
| AL | | | | | | | |
| AM | | | | | | | |
| AN | | | | | | | |
| AO | | | | | | | |
| AP | | | | | | | |

OTHER (Including Author, Title, Date, Pertinent Pages, Etc.)

| AR | Richard H. Farris & Charles Lee, "Determination of Time Independent Component of the Complex Modulus During Cure of |
| AS | Thermosetting Systems", POLYMER ENGINEERING AND SCIENCE, July, 1983, Vol. 23, No. 10 |
| AT | Richard J. Farris, "An Impulse Approach to Linear Viscoelasticity" POLYMER SCIENCE & ENGINEERING, University of Mass, 1983 |

Signed and Sealed this

Twenty-fourth Day of December, 1991

Attest:

HARRY F. MANBECK, JR.

*Attesting Officer*                     *Commissioner of Patents and Trademarks*